United States Patent [19]

Nishio

[11] Patent Number: 5,042,483
[45] Date of Patent: Aug. 27, 1991

[54] NONCONTACT TYPE TONOMETER

[75] Inventor: Kouji Nishio, Tokyo, Japan

[73] Assignee: Kabushiki Kaisha Topcon, Tokyo, Japan

[21] Appl. No.: 569,741

[22] Filed: Aug. 21, 1990

Related U.S. Application Data

[63] Continuation of Ser. No. 340,191, Apr. 19, 1989, abandoned.

[30] Foreign Application Priority Data

Apr. 21, 1988 [JP] Japan .................................. 63-98796

[51] Int. Cl.$^5$ .............................................. A61B 3/16
[52] U.S. Cl. ....................................... 128/648; 128/652
[58] Field of Search ............... 128/645, 646, 647, 648, 128/652

[56] References Cited

U.S. PATENT DOCUMENTS 4,172,447 10/1979 Bencze et al. ........................ 128/648
4,872,460 10/1989 Nishio et al. ........................ 128/648

Primary Examiner—Randy C. Shay
Attorney, Agent, or Firm—Finnegan, Henderson, Farabow, Garrett & Dunner

[57] ABSTRACT

In a noncontact type tonometer including an air puff system for discharging fluid toward the cornea of an eye to be tested upon receipt of a projection signal and a pulse wave system for detecting the pulse of a patient which outputs an alternating voltage, the improvement comprising zero level detection system for detecting a zero level of the alternating voltage; and a timer which starts counting when the zero level has been detected by the zero detection systems and which outputs a projection signal to actuate the air puff system when the counted value has reached a preset time.

9 Claims, 4 Drawing Sheets

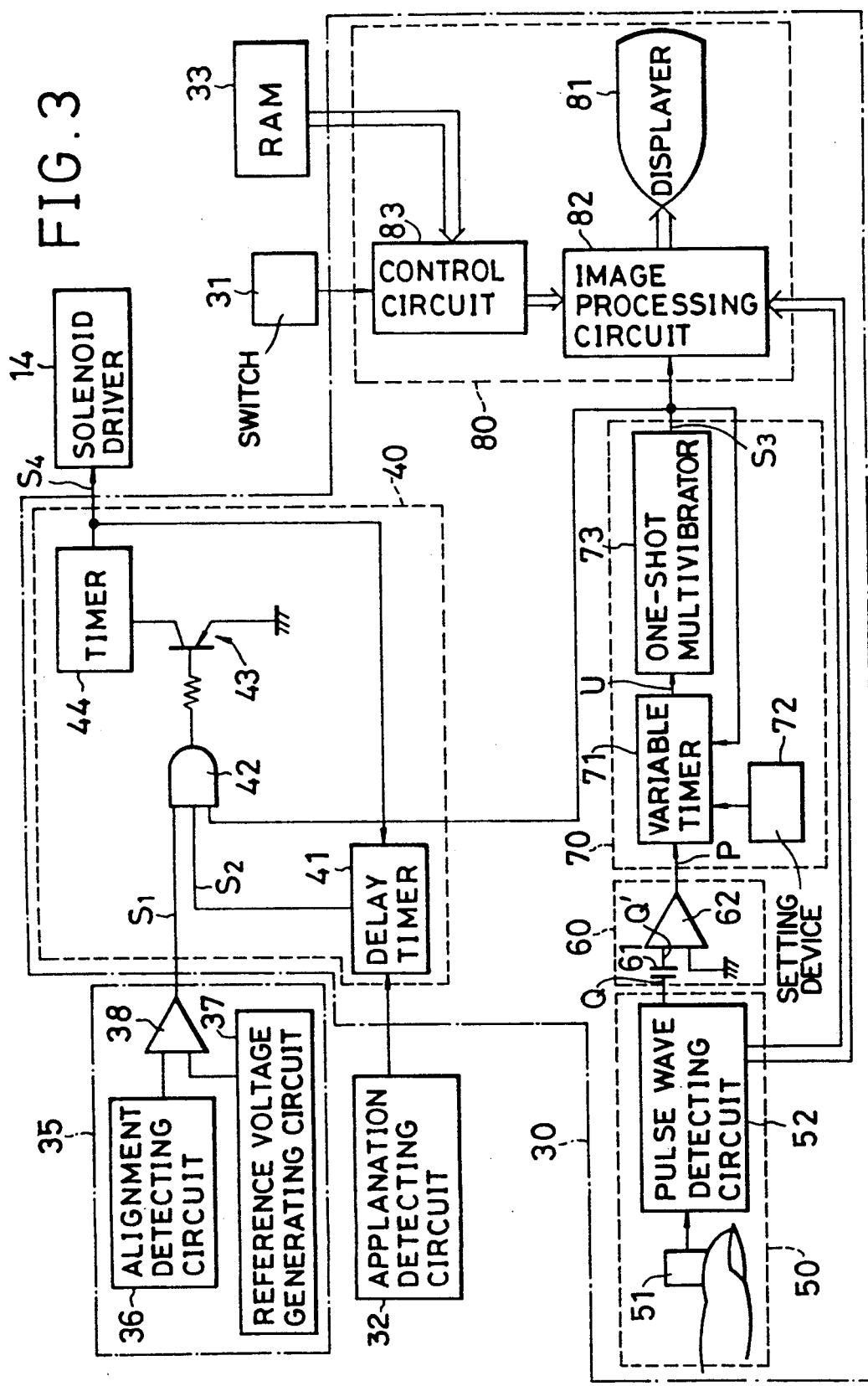

NONCONTACT TYPE TONOMETER

This application is a continuation of application Ser. No. 07/340,191, filed Apr. 19, 1989, now abandoned.

BACKGROUND OF THE INVENTION

1. Field of the Invention

This invention relates to an improvement of a noncontact type tonometer which is designed to improve the reliability of intraocular pressure measurement while taking into consideration the fluctuation of intraocular pressure due to pulse fluctuation. More particularly, it relates to a noncontact type tonometer including means for discharging fluid toward the cornea of an eye to be tested (hereinafter simply referred to as the "eye") upon receipt of a projection signal, and means for detecting the pulse wave of a patient and outputting alternating voltage corresponding to such detected pulse wave.

2. Description of the Related Art

As a conventional tonometer, there is a tonometer of a noncontact type, such as an air puff type, wherein a fluid pulse is discharged toward the eye of a patient and intraocular pressure of the eye is measured from the relation between the transfiguration of the cornea of the eye and the pressure of the fluid discharged. In the tonometer of this type, an air pulse is instantaneously discharged toward the eye in a short period of time such as, several tens of milliseconds and the cornea is transfigured (for example, applanation) in such a very short period of time as several ms to measure the intraocular pressure.

In general, intraocular pressure fluctuates in accordance with the fluctuation of the pulse. The maximum fluctuation of the intraocular pressure is several mmHg. The intraocular pressure of a normal human eye is usually 10 mmHg~20 mmHg. Also, the human pulse is usually 60 times/min.~120 times/min., and the cycle of the fluctuation of the intraocular pressure is at least approximately 50 ms. Therefore, if the measurement of the intraocular pressure is carried out without taking into consideration the fluctuation of the intraocular pressure due to the pulse, the value of such measured intraocular pressure could become correspondingly higher if the measurement is carried out at the peak of the pulse wave. Similarly the value of such measured intraocular pressure could become correspondingly lower if the measurement is carried out at the valley of the pulse pressure wave (sphygmogram). Therefore, if the fluctuation of the intraocular pressure due to the pulse is not taken into consideration, the reliability of the measurement would become lower.

Therefore, there has been proposed a tonometer for measuring intraocular pressure while adjusting for the pulse (U.S. Pat. No. 3,572,100 issued Mar. 23, 1971). The tonometer disclosed in this Patent Publication is designed such that the measurement of the intraocular pressure is always carried out at the same phase position of the pulse wave. According to this tonometer, measuring errors caused by the fluctuation of the pulse can be removed.

In this tonometer, however, since one cycle of the pulse is divided into five equal parts and the measurement of the intraocular pressure is carried out in synchronism with a single selected phase position out of such divided five equal parts, the measurement cannot be carried out in synchronism with a desired phase position other than such divided five equal phase positions.

Generally speaking, a noncontact type tonometer requires strict accuracy in alignment of the tonometer with respect to the eye. In order to carry out the measurement with high accuracy, for example, the vertical or horizontal position of a fluid discharging nozzle (hereinafter simply referred to as the "nozzle") with respect to the eye, i.e., the working distance from the eye to the tip of the nozzle, requires strict accuracy in alignment. The tolerance in alignment is required to be less than one mm from a correct alignment position. With the above-mentioned tonometer, however, since the measurement of the intraocular pressure is carried out in synchronism with the selected phase of the pulse irrespective of correctness of the alignment, the measuring accuracy is lowered.

SUMMARY OF THE INVENTION

A first object of the present invention is to provide a noncontact type tonometer capable of measuring the intraocular pressure of an eye to be tested in synchronism with a desired phase position of the pulse wave.

A second object of the invention is to provide a noncontact type tonometer capable of displaying the pulse wave and the position of the pulse wave where the measurement is carried out.

A third object of the invention is to provide a noncontact type tonometer capable of carrying out the measurement in synchronism with the phase position of the pulse wave only when the proper alignment has been verified.

One feature of the present invention comprises
zero detection means for detecting a zero level of the alternating voltage; and
timer means for counting when the zero level has been detected by the zero detection means and outputting a projection signal in order to actuate the fluid discharging means when the counted time has reached a preset time.

Another feature of the present invention comprises
zero level detection means for detecting a zero level of the alternating voltage;
timer means for counting when the zero level has been detected by the zero detection means and outputting a projection signal in order to actuate the fluid discharging means when the counted time has reached a preset time; and
displayer means for displaying the pulse wave according to the alternating voltage output from the pulse wave detection means and the outputting time of the projection signal.

A further feature of the present invention comprises
pulse wave synchronizing means for outputting a pulse wave synchronizing signal in synchronism with a desired phase position of the pulse wave detected by the pulse wave detection means; and
projection signal outputting means for outputting a projection signal upon receipt of the pulse wave synchronizing signal and an alignment signal in order to actuate the fluid discharging means.

A still further feature of the present invention comprises
pulse wave synchronizing means for outputting a pulse wave synchronizing signal in synchronism with a desired phase position of the pulse wave detected by the pulse wave detection means;

projection signal outputting means for outputting a projection signal upon receipt of the pulse wave synchronizing signal and an alignment signal in order to actuate the fluid discharging means; and displayer means for displaying the pulse wave according to the alternating voltage output from the pulse wave detection means and the outputting time of the pulse wave synchronizing signal.

A yet further feature of the present invention comprises zero level detection means for detecting a zero level of the alternating voltage;

pulse wave synchronizing means for start counting when the zero level has been detected by the zero detection means and outputting a pulse wave synchronizing signal when the counted time has reached a desirably preset time; and projection signal outputting means for outputting a projection signal upon receipt of the pulse wave synchronizing signal and an alignment signal in order to actuate the fluid discharging means.

BRIEF DESCRIPTION OF THE DRAWINGS

FIG. 3 is a block diagram showing an embodiment of a control unit;

DETAILED DESCRIPTION OF THE PREFERRED EMBODIMENTS

One embodiment of the present invention will be described hereunder with reference to the accompanying drawings.

Figure 1:
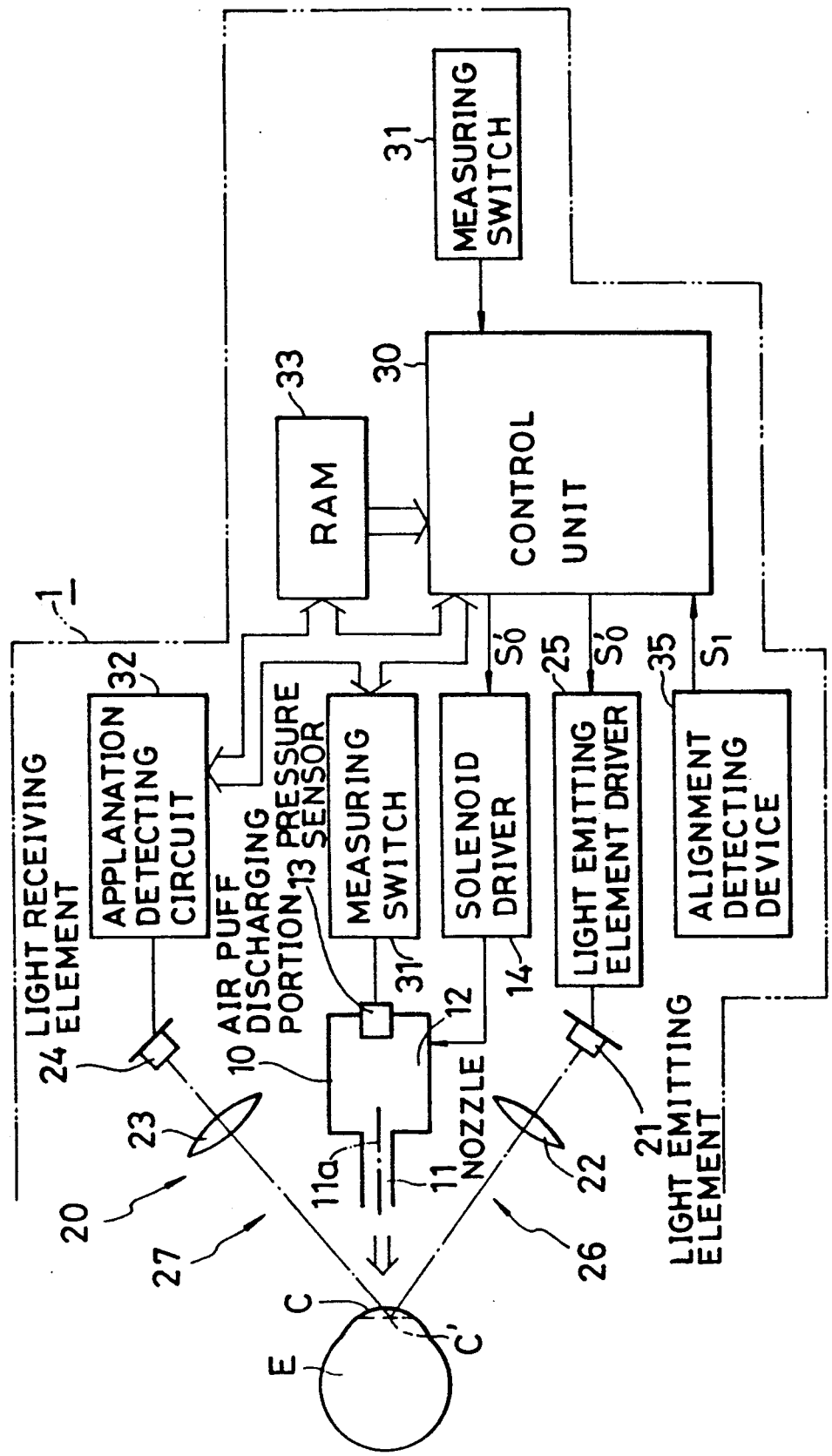
FIG. 1 is a block diagram showing an embodiment of a noncontact type tonometer according to the present invention.

In FIG. 1, 1 denotes an intraocular pressure measuring portion, which is described in detail in Japanese Patent Application No. Sho 59-242279 (Japanese Patent Application Early Laid-open Publication No. Sho 61-122839) filed by the present applicant. The intraocular pressure measuring portion 1 includes an air puff discharging portion 10 adapted to discharge fluid, such as air, etc., toward the cornea C of eye E in order to transfigure the cornea C, a corneal transfiguration detecting system 20 adapted to detect the configuration of the cornea C, and a control unit 30 adapted to control a solenoid driver 14, a light emitting driver 25, etc.

The air puff discharging portion 10 includes a nozzle 11 for discharging fluid toward the cornea C, an air chamber 12, and a piston and a cylinder (not shown). 13 denotes a pressure sensor for measuring air pressure within the air chamber 12. The piston is actuated by a solenoid (not shown), and the solenoid is excited by a solenoid driver 14. When the piston is actuated by the solenoid, air within the cylinder is compressed and fed to the air chamber 12 under pressure and then, the compressed air within the air chamber 12 is discharged toward the eye E. A fluid discharging means comprises the air puff discharging portion 10 and the solenoid driver 14.

The corneal transfiguration detecting system 20 comprises a projecting optical system 26 and a light receiving optical system 27 which are symmetrically disposed with respect to the axial line 11a of the nozzle 11. The projecting optical system 26 comprises a light emitting element 21 for emitting light and a projecting lens 22 for projecting the emitted light toward the cornea C in form of parallel pencil of rays. The light receiving optical system 27 comprises an imaging lens 23 for condensing the flux of light reflected by the cornea C and a light receiving sensor 24 disposed such that its light receiving plane is located at the condensing point of the imaging lens.

31 denotes a measurement start switch for causing the control unit 30 to begin a measuring step. Upon actuation of the measurement start switch 31, the control unit 30 causes the light emitting element driver 25 to be actuated and also causes the solenoid driver 14 to be activated when the conditions described hereinafter are satisfied. Upon actuation of this solenoid driver 14, the piston is activated to raise the pressure of air within the air chamber 12. The pressure is sequentially detected by the pressure sensor 13 and the detected power output is input into the pressure detecting circuit 31 as detected pressure data. This detected pressure data corresponds to the positive force of air discharged from the nozzle 11.

On the other hand, the quantity L of light reflected from the cornea C is sequentially detected by the light receiving element 24 during the process where the cornea C is transfigured by a predetermined amount, and the reflected light quantity based on the corneal reflected light quantity L is input into an applanation detecting circuit 32. The applanation detecting circuit 32 converts the reflected light quantity signal to a reflected light quantity data in the form of a digital signal corresponding to the signal value. RAM 33 stores the reflected light quantity data therein.

Figure 2:
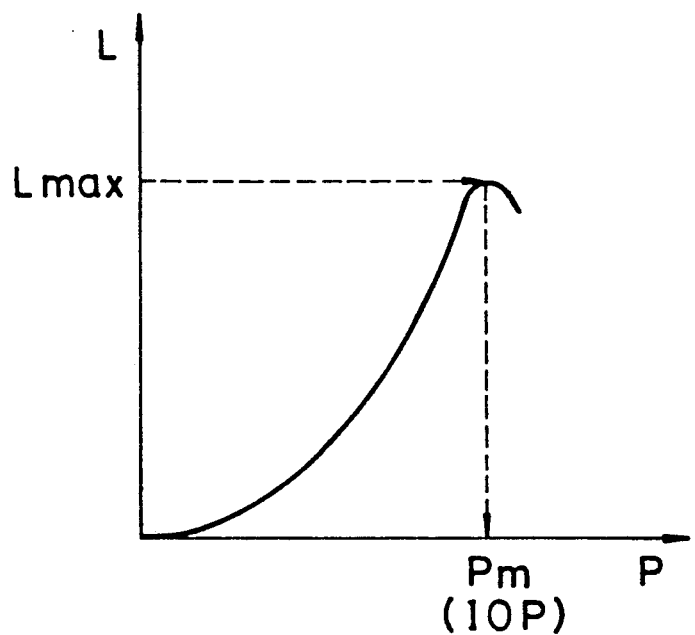
FIG. 2 is a schematic view showing the relation between the pressure of air puff and the light received quantity of a light receiving element.

In the RAM 33, addresses are renewed every time the detected pressure data of the applanation detecting circuit 31 is raised by a predetermined unit pressure with reference to the predetermined unit pressure as a scale (i.e., addresses and pressure are corresponded with each other), and the reflected light quantity data from the applanation detecting circuit 32 is stored in each address. By this, the RAM 33 stores the pressure-light quantity function by taking the detected pressure P on the horizontal axis and by taking the corneal reflected light quantity L on the vertical axis is shown in FIG. 2. The control unit 30 finds intraocular pressure 10P from the pressure-light quantity function stored in the RAM 33 based on the detected pressure data Pn (address) corresponding to the corneal reflected light quantity L of the maximum Lmax due to planar applanation (see reference character C' of FIG. 1) of the cornea C.

35 denotes an alignment detecting device (alignment detection means) for detecting alignment of the nozzle 11 with respect to the eye E. The alignment detecting device is described in detail in U.S. Pat. No. 4,665,923 issued on May 19, 1987, assigned to same assignee of this application. The alignment detecting device 35 functions cooperatively with target image projecting optical system, etc. (not shown) adapted to project a target image to the eye E to form a target image thereon. As shown in FIG. 3, the alignment detection device 35 comprises an alignment detecting circuit 36 for outputting a target image detected signal upon receipt of the target image, a reference voltage generating circuit 37 for outputting a reference voltage in order to determine whether the alignment of the nozzle 11 has been verified with respect to the eye E, and a comparator 38 for comparing the target image detected signal with the reference voltage and outputting an alignment completion signal $S_1$ of H-level when the target image detected signal becomes the reference voltage or less.

The control unit 30, as shown in FIG. 3, comprises a projection signal outputting portion (projection signal outputting means) 40 for outputting a projection command signal $S_4$ (projection signal) in order to actuate the solenoid driver 14, a pulse wave detecting portion (pulse wave detection means, or sphygmograph) 50 for detecting the pulse wave (or sphygmogram) of a patient, a zero level detecting portion (zero level detection means) 60 for detecting a zero level point of the pulse wave, a synchronizing signal generating portion (pulse wave synchronizing means) 70 for outputting a synchronizing signal $S_3$ in synchronism with a desired phase position of the pulse wave, and a control portion 80 for finding intraocular pressure, etc.

The projection signal outputting portion 40 comprises an AND circuit 42 into which an alignment completion signal output from the alignment detecting device 35, a delay signal output from the delay timer 41 and a synchronizing signal $S_3$ output from the synchronizing signal generating portion 70 are input, a transistor 43 which conducts upon the application of an H-level signal output from the AND-circuit, and a timer 44 actuated by the conduction of the transistor 43.

This timer 44 used herein is a power only set type, which starts counting every time the transistor 43 conducts. The timer 44 is set as such that the counting is made only when the timer 44 is being conducted and the counting is stopped when it is not conducted.

After counting for a predetermined period of time, this timer 44 outputs the projection command signal $S_4$ toward the solenoid driver 14 and the delay timer 41 in order to start discharging fluid. The predetermined period of time is set to 0.2 seconds in this embodiment taking into consideration the fixation flick or tremor of the eye. Upon input of the projection command signal $S_4$, the solenoid driver 14 automatically discharges fluid. By this, an air pulse is discharged onto the cornea of the eye.

Even if the alignment completion signal $S_1$ is output in spite of incorrect alignment due to accidental reasons such as patient's looking aside, fixation flick or tremor, etc. from the comparator 38, the alignment completion signal $S_1$ can remain in its H-level only momentarily, i.e., less than 0.2 seconds. Therefore, the alignment completion signal $S_1$ becomes L-level the next moment, and the transistor 43 becomes non-conductive in the midway of the predetermined period of counting time. Therefore, since the timer 44 is reset and the projection command signal $S_4$ is not output, intraocular pressure measurement, which is based on accidental reasons such as fixation flick or tremor, can be avoided.

The pulse wave detector (or sphygmograph) 50 comprises a transducer 51 adapted to output voltage corresponding to the pressure of the pulse wave of a patient and a pulse wave detecting circuit 52 adapted to output a pulse wave signal corresponding to the voltage output from this transducer 51.

The zero level detecting portion 60 comprises a condenser 61 adapted to block the direct current portion of a pulse wave signal and a comparator 62 adapted to compare the voltage of the pulse wave signal with a ground voltage (zero voltage) and output a comparison signal of H-level when the voltage of the pulse wave signal is more than the ground voltage.

The synchronizing signal generating portion 70 comprises a variable timer 71 adapted to start counting when a comparison signal P output from the comparator 62 rises, a setting device adapted to desirably set the period of counting time of the variable timer 71 and a one-shot multivibrator 73 adapted to output a synchronizing signal $S_3$ of H-level upon receipt of a signal output from the variable timer 71. After counting down the predetermined counting time set by the setting device 72, the variable timer 71 outputs an H-level signal and is reset upon receipt of the synchronizing signal $S_3$ of H-level output from the one-shot multivibrator 73. The variable timer 71 and the setting device 72 comprises the counting means.

Figure 5:
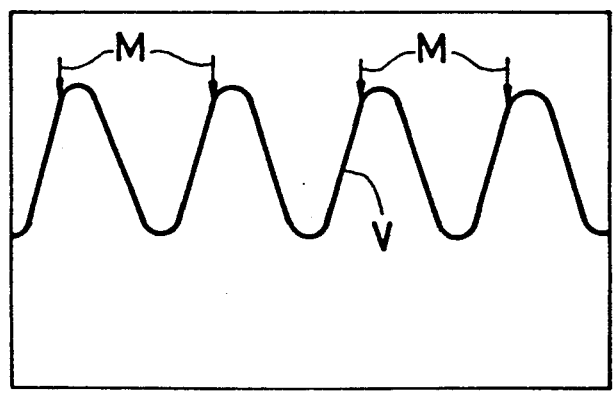
FIG. 5 is a schematic view of pulse wave.

The control portion 80 comprises a displayer 81 for displaying the pulse wave (or sphygmogram) V, as shown in FIG. 5, upon receipt of a pulse wave signal of the pulse wave detecting circuit 52, an image processing circuit 82 for displaying an arrow (mark) M in phase position of the pulse wave V at the time point when the synchronizing signal $S_3$ is output and a control circuit 83 for finding the intraocular pressure of the eye E from the data stored in the RAM 33 and controlling the circuits 14, 25, etc.

The delay timer 41 includes a normal closed contact (not shown) which, when the delay timer 41 is not counting, is closed to output an inhibiting signal $S_2$ of H-level and which, when the delay timer 41 is counting, is opened to output an inhibiting signal $S_2$ of L-level.

Also, the delay timer 41 starts counting when the applanation signal output from the applanation detecting circuit 31 becomes maximum. The delay timer 41 functions as delaying means such that a second discharge of fluid will be delayed for a predetermined interval of time from when a first discharge of fluid is made so that the second discharge of fluid is inhibited for the predetermined interval of time. The predetermined interval of time for the delay timer 41 is set to $2 \sim 5$ seconds in this embodiment taking into consideration the time required for intaking a desired capacity of air into a cylinder of an apparatus (not shown) of the air puff discharging portion 10. Also, the delay timer 41 stops counting after passage of the predetermined time to make the normal closed contact from open to close. When the normal closed contact is in its open position, the inhibiting signal $S_2$ output from the delay timer 41 inhibits the timer 44 from starting the counting for performing the second fluid discharge for a predetermined time. That is, the delay timer 41 prevents incomplete discharge of fluid in sequence.

Next, the function of the above-mentioned embodiment will be described with reference to FIG. 4.

Figure 4:
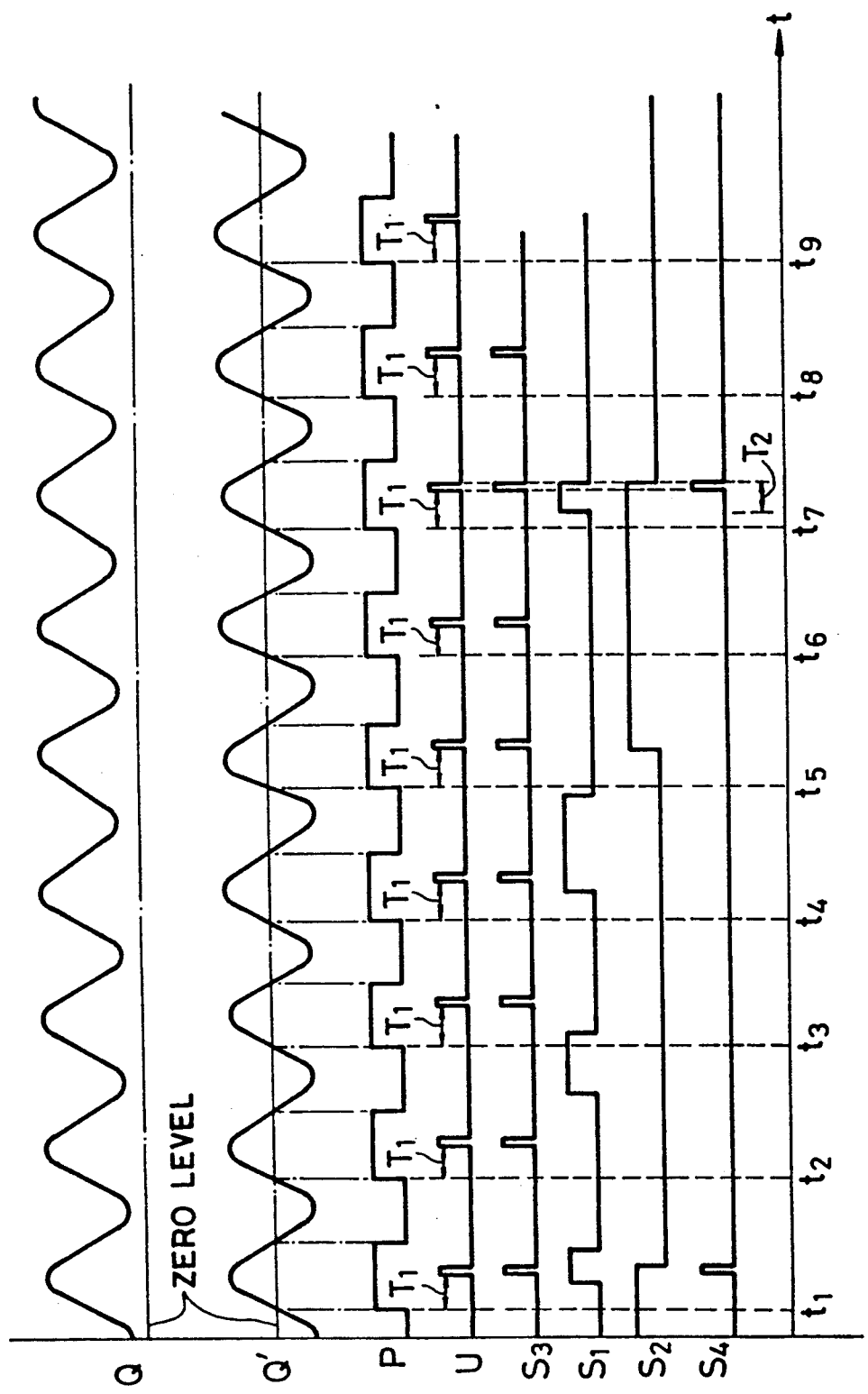
FIG. 4 is a timing chart for signals output from various circuits.

When power corresponding to the pressure of the pulse wave of the patient is output from the transducer 51, a pulse wave signal Q corresponding to the voltage is output from the pulse wave detecting circuit 52 as shown in FIG. 4 and the direct current portion of the pulse wave signal Q is blocked by the condenser 61 and compared with the ground voltage. When a pulse wave Q', from which the direct current portion is blocked, reaches the ground voltage or more, a comparison signal P of H-level is output from the comparator 62 and the variable timer 71 begins counting the rise of the comparison signal P.

That is, the variable timer 71 is activated for counting from the time points ($t_1 \sim t_9$) where the pulse wave signal Q' is at a zero level point. When this counting reaches a counting time $T_1$ desirably preset by the setting device 72, a timer signal U is output from the variable timer 71 and input into the one-shot multivibrator 73. Then, the synchronizing signal $S_3$ is output from this one-shot multivibrator 73 and input into the AND circuit 42.

When the AND circuit 42 is input with the alignment completion signal $S_1$ output from the comparator 38 and the inhibiting signal $S_2$ of H-level output from the delay timer 41 (when it is T term of FIG. 4), a signal of H-level is output from the AND circuit 42 upon input of the synchronizing signal $S_3$ and as a result, the transistor 43 is conducted. Due to this conduction, the timer 44 is actuated and outputs the projection command signal $S_4$ of H-level 0.2 seconds after this actuating time point (FIG. 4 shows the projection command signal $S_4$ omitting this 0.2 seconds). The solenoid driver 14 is actuated by this projection command signal $S_4$ and an air pulse is discharged from the nozzle 11 to measure the intraocular pressure of the eye E.

Since the outputting time point of the synchronizing signal $S_3$ can be desirably set by varying the counting time of the variable timer 71 using the setting device 72, an air puff can be discharged at the desired phase position of the pulse wave. Thereby the intraocular pressure can be measured in every possible situation. Also, the alignment completion signal $S_1$ is not input into the AND circuit 42 from the comparator 38 as long as the alignment is not verified yet. Therefore, no signal of H-level is output from the AND circuit and no projection command signal $S_4$ is output from the timer 44. That is, since no air puff is discharged toward the eye E from the nozzle 11 before the verification of the alignment, and it is discharged only after the verification thereof, a correct intraocular pressure can always be measured.

Also, since the displayer 81 is displayed thereon with the pulse wave V and the arrow M in the phase position of the pulse wave V, the inspector can set the synchronizing signal $S_3$ to a desired phase position of the pulse wave V by looking the displayer 81. Therefore, inspector can perform the measurement of the intraocular pressure with ease.

As described in the foregoing, according to the present invention, the outputting time of the projection signal can be set to desired phase position of the pulse wave by looking at the displayer means, and the projection signal can be output in the desirably set phase position in order to actuate the fluid discharging means. Accordingly, measurement of the intraocular pressure can be performed in every possible situation and the correlation between the phase of the pulse wave and the intraocular pressure can more correctly obtained.

Also, the fluid discharging means is actuated by outputting the projection signal only after the verification of the alignment. Accordingly, a correct intraocular pressure can always be measured.

What is claimed is:

1. In a noncontact type tonometer including means for discharging fluid toward the cornea of an eye to be tested upon receipt of a projection signal and means for detecting a pulse wave of a patient in order to output an alternating voltage, the improvement comprising:
   zero detection means for detecting a zero level of the alternating voltage; and
   timer means for starting counting when the zero level has been detected by said zero detection means and for outputting a projection signal in order to actuate said fluid discharging means when the counted time has reached a preset time.

2. In a noncontact type tonometer including means for discharging fluid toward the cornea of an eye to be tested upon receipt of a projection signal and means for detecting the pulse wave of a patient in order to output an alternating voltage, the improvement comprising:
   zero level detection means for detecting a zero level of the alternating voltage;
   timer means for starting counting when the zero level has been detected by said zero detection means and for outputting a projection signal in order to actuate said fluid discharging means when the counted time has reached a preset time; and
   displayer means for displaying the pulse wave according to the alternating voltage output from said pulse wave detection means and the outputting time of the projection signal.

3. A noncontact type tonometer according to claim 2, wherein said displayer means includes an image processing circuit for superimposing the alternating voltage output from said pulse wave detection means and a mark showing the outputting time of the projection signal one upon the other, and a displayer for displaying the alternating voltage and the mark superposed one upon the other by said image processing circuit.

4. In a noncontact type tonometer including means for discharging fluid toward the cornea of an eye to be tested upon receipt of a projection signal, means for detecting a pulse wave of a patient and alignment detection means for outputting an alignment signal upon detecting alignment between the eye and a nozzle of the fluid discharging means, the improvement comprising:
   pulse wave synchronizing means for outputting a pulse wave synchronizing signal in synchronism with a desired phase position of the pulse wave detected by said pulse wave detection means; and
   projection signal outputting means for outputting a projection signal upon receipt of the pulse wave synchronizing signal and the alignment signal in order to actuate said fluid discharging means.

5. In a noncontact type tonometer including means for discharging fluid toward the cornea of an eye to be tested upon receipt of a projection signal, means for detecting a pulse wave of a patient in order to output an alternating voltage, and alignment detection means for outputting an alignment signal upon detecting alignment between the eye and a nozzle of the fluid discharging means, the improvement comprising:
   pulse wave synchronizing means for outputting a pulse wave synchronizing signal in synchronism with a desired phase position of the pulse wave detected by said pulse wave detection means;
   projection signal outputting means for outputting a projection signal upon receipt of the pulse wave synchronizing signal and the alignment signal in order to actuate said fluid discharging means; and
   displayer means for displaying the pulse wave according to the alternating voltage output from said pulse wave detection means and the outputting time of the pulse wave synchronizing signal.

6. A noncontact type tonometer according to claim 5, wherein said displayer means includes an image processing circuit for superposing the alternating voltage output from said pulse wave detection means and a mark showing the outputting time of the synchronizing signal one upon the other and a displayer for displaying the alternating voltage and the mark superposed one upon the other by said image processing circuit.

7. In a noncontact type tonometer including means for discharging fluid toward the cornea of an eye to be tested upon receipt of a projection signal, means for detecting a pulse wave of a patient in order to output an alternating voltage, and alignment detection means for outputting an alignment signal upon detecting alignment between the eye and a nozzle of the fluid discharging means, the improvement comprising:

zero level detection means for detecting a zero level of the alternating voltage;

pulse wave synchronizing means for starting counting when the zero level has been detected by the zero detection means and outputting a pulse wave synchronizing signal when the counted time has reached a preset time; and projection signal outputting means for outputting a projection signal upon receipt of the pulse wave synchronizing signal and the alignment signal in order to actuate said fluid discharging means.

8. A noncontact type tonometer according to claim 7, wherein said pulse wave synchronizing means includes a timer which starts counting from the time when the zero level is detected and a one-shot multivibrator for outputting a pulse wave synchronizing signal when the time counted by said timer reaches the desirably preset time.

9. A noncontact type tonometer according to claim 5 or claim 7, wherein said projection signal outputting means includes an AND circuit, into which the pulse wave synchronizing signal and the alignment signal can be input, for outputting an AND signal when the pulse wave synchronizing signal and the alignment signal are input simultaneously, and a timer which counts during a period of time when the AND signal is being output from said AND circuit for outputting the projection signal when the counted time reaches a preset counting time.

* * * * *